US008666935B2

(12) United States Patent
Evanitsky (10) Patent No.: US 8,666,935 B2
(45) Date of Patent: Mar. 4, 2014

(54) SYSTEM AND METHOD OF ON-DEMAND DOCUMENT PROCESSING FOR A MEDICAL OFFICE

(75) Inventor: Eugene Stephen Evanitsky, Pittsford, NY (US)

(73) Assignee: Xerox Corporation, Norwalk, CT (US)

( * ) Notice: Subject to any disclaimer, the term of this patent is extended or adjusted under 35 U.S.C. 154(b) by 631 days.

(21) Appl. No.: 12/401,176

(22) Filed: Mar. 10, 2009

(65) Prior Publication Data

US 2010/0235369 A1    Sep. 16, 2010

(51) Int. Cl.
G06F 7/00 (2006.01)
G06F 17/00 (2006.01)
G06F 12/00 (2006.01)
G06F 17/30 (2006.01)

(52) U.S. Cl.
USPC .......................................... 707/608; 707/821

(58) Field of Classification Search
USPC ................................................ 707/608, 821
See application file for complete search history.

(56) References Cited

U.S. PATENT DOCUMENTS

| 4,965,763 | A | 10/1990 | Zamora |
| 6,043,819 | A | 3/2000 | LeBrun et al. |
| 7,389,144 | B1 * | 6/2008 | Osorio et al. .................... 607/29 |
| 2001/0044732 | A1 * | 11/2001 | Maus et al. ......................... 705/3 |
| 2002/0067497 | A1 | 6/2002 | Thieret et al. |
| 2005/0120300 | A1 * | 6/2005 | Schwager et al. ............. 715/513 |
| 2005/0288965 | A1 * | 12/2005 | Van Eaton et al. ................ 705/2 |
| 2006/0005139 | A1 * | 1/2006 | Comaniciu et al. ........... 715/760 |
| 2007/0282632 | A1 | 12/2007 | Sachs |
| 2008/0082352 | A1 * | 4/2008 | Schmidtler et al. ............... 705/1 |
| 2008/0301120 | A1 | 12/2008 | Zhu et al. |
| 2009/0024637 | A1 | 1/2009 | Krishna et al. |
| 2009/0070380 | A1 * | 3/2009 | Schwager et al. ......... 707/104.1 |
| 2009/0220153 | A1 * | 9/2009 | Hall et al. ...................... 382/181 |
| 2010/0235305 | A1 | 9/2010 | Evanitsky et al. |

* cited by examiner

Primary Examiner — Apu Mofiz
Assistant Examiner — Jared Bibbee
(74) Attorney, Agent, or Firm — Fay Sharpe LLP (57) ABSTRACT

A document processing method for a medical office includes receiving, at a server with a network interface, electronic documents from a medical office. The server includes a software application adapted to recognize an expected class of electronic documents corresponding to the medical office. The method also includes processing the electronic documents received from the medical office to extract data therefrom based on a recognition that the electronic documents belong to the expected class of electronic documents corresponding to the medical office. The method also includes automatically mapping the extracted data from the processed electronic documents to a data repository on the server. The data repository is accessible by the medical office through the network interface. The method also includes monitoring a behavior of the medical office based on access to the mapped data and electronically generating output data to the medical office based on the mapped data on the data repository and/or the monitored behavior of the medical office. The output data corresponds to operation of the medical office.

19 Claims, 4 Drawing Sheets

SYSTEM AND METHOD OF ON-DEMAND DOCUMENT PROCESSING FOR A MEDICAL OFFICE

BACKGROUND

1. Technical Field

The present disclosure relates to document processing, and, in particular, to a system and method of on-demand document processing for a medical office.

2. Description of Related Art

Document processing, for most entities, is an expensive and time consuming process because of the need for customization, dedicated resources, and long sales cycles. Currently-used systems typically work well for large entities, however, small to medium sized entities also have a need for document processing systems. In particular, small to medium sized medical offices must handle a large amount of paper documents on a daily basis. In addition to handling a large volume of paper documents, medical offices must not only handle documents related to patients, but documents related to the day-to-day operations of the office as well. Further, protection and privacy of documents in the medical office setting is paramount due to the sensitive nature of certain documents and the laws with which the medical industry must comply (e.g., Sarbanes Oxley). This handling of documents is costly in terms of both time and money and, as a result, interferes with what should be the primary function of a medical office, namely, caring for patients.

Many of the tools required to process and manage digital information are costly and require specific expertise for effective use. Systems to store and transfer data securely are also costly to own and are often complicated to use. Currently, there are a variety of companies that offer small business software applications, provide related IT support or ISP, provide payroll services, and provide legal services. Still, other services provide systems to store, share, and access documents, however, these services do not provide for a system that automatically classifies documents and/or extracts metadata therefrom. Nor do these services provide a system that processes specific document types that can be recognized and from which data can be extracted and mapped to a data repository.

SUMMARY

According to an embodiment of the present disclosure, a document processing method for a medical office includes receiving, at a server with a network interface, electronic documents from a medical office. The server includes a software application adapted to recognize an expected class of electronic documents corresponding to the medical office. The method also includes processing the electronic documents received from the medical office to extract data therefrom based on a recognition that the electronic documents belong to the expected class of electronic documents corresponding to the medical office. The method also includes automatically mapping the extracted data from the processed electronic documents to a data repository on the server. The data repository is accessible by the medical office through the network interface. The method also includes monitoring a behavior of the medical office based on access to the mapped data and electronically generating output data to the medical office based on the mapped data on the data repository and/or the monitored behavior of the medical office. The output data corresponds to operation of the medical office.

According to another embodiment of the present disclosure, a document processing system for a medical office includes a document services grid accessible through a network interface. The document services grid is adapted to receive electronic documents from a medical office through the network interface. The document services grid includes a hosted server including a software application adapted to recognize expected electronic documents corresponding to the medical office. The document services grid also includes a data repository operating on the hosted server. The data repository is configured to store data automatically mapped from the processed electronic documents based on a recognition thereof. The mapped data corresponds to operation of the medical office. The document services grid is configured to generate output data to the medical office based on the mapped data.

According to another embodiment of the present disclosure, a document processing method for a medical office includes receiving, at a server, electronic documents from a medical office. The server is hosted on a document services grid accessible through a network interface. The document services grid includes a software application adapted to recognize an expected class of electronic documents corresponding to the medical office. The method also includes processing electronic documents received from the medical office through the network interface based on a recognition that the electronic documents belong to the expected class of electronic documents corresponding to the medical office. The method also includes automatically mapping data from the processed electronic documents to a data repository on the hosted server and monitoring a behavior of the medical office based on access to the mapped data. The method also includes generating reports based on the mapped data and/or the monitored behavior of the medical office. The reports correspond to operation of the medical office and are accessible by the medical office via the network interface.

BRIEF DESCRIPTION OF THE DRAWINGS

These and other advantages will become more apparent from the following detailed description of the various embodiments of the present disclosure with reference to the drawings wherein.

DETAILED DESCRIPTION

Embodiments of the presently disclosed scaleable integration framework will now be described in detail with reference to the drawings in which like reference numerals designate identical or corresponding elements in each of the several views.

The present disclosure relates to an online service, and, in particular, to a system and method for creating specific document intensive services for well understood, repeatable processes used in medical offices. Medical offices may include, for example without limitation, doctors, dentists, chiropractors, veterinarians, rehab clinics, and the like. The system utilizes basic internet technologies, readily available image capture devices, and trained document processing tools that utilize knowledge specific to the medical industry to provide services to medical offices in an intuitive, low cost of entry/exit model that can be provided to meet a medical office's maturity level. The system is scaleable in that services may be provided to various sizes of businesses in the medical industry. More specifically, the system has the scalability to provide services to a small to medium sized medical office and/or to provide services individually to each of a plurality of small to medium sized medical offices. With this purpose in mind, the system utilizes a document services grid ("DSG") including a hosted server accessible over the Internet through an intuitive web-based interface or customer web portal to combine document processing capabilities (e.g., categorization, extraction, etc.) with continuous learning capability (e.g., by example, training, and continuous updating). The DSG utilizes trained document processing tools to receive and process electronic documents of a specific type (e.g., insurance forms, patient medical records, doctors notes, prescriptions, office billing, office and equipment maintenance, tax and privacy compliance, etc.). Electronic documents are sent via the Internet through a web-based interface from a medical office (or from a user associated with the medical office) to the DSG wherein data (or metadata) is extracted from the electronic documents and subsequently recognized or classified and mapped to a data repository on the hosted server. The DSG may be pre-configured with rules specific to the medical industry (e.g., Sarbanes Oxley compliance, insurance, HIPPA, etc.) that dictate the specific data extracted from a particular processed electronic document.

The customer (e.g., office administrator, nurse, attendant, etc.) is able to securely access the data repository through the web-based interface to verify, and if necessary, correct the resulting data extraction and/or document classification and store the verified and/or corrected results in the data repository on the hosted server. Thereafter, subsequently processed electronic documents of the same and/or substantially similar class as electronic documents that have been verified and/or corrected, are recognized by the system and automatically classified without the need for further verification and/or correction. In this manner, the DSG is self-learning in that each successful classification and extraction related to a processed electronic document enables the system to accumulate a so-called "knowledge-base" of documents specific to the medical office industry to continuously improve document recognition and/or classification accuracy, thereby progressing the maturation process of the service for both the DSG and the medical office that is using the service. Documents may be redacted by the system based on the credentials of the viewer to protect privacy. Further, the DSG monitors and analyzes usage of the service and prompts the service manager or administrator to invest in more capacity or greater automation for heavily used services.

The DSG is adapted to monitor and analyze its own document recognition and/or classification success rate as well as the behavior of the medical office using the service. In this way, the DSG intelligently and dynamically provides recommendations to the customer related to modifying and improving the customer's work practices. Specifically, the DSG monitors for process maturity indicators such as, for example, multiple users looking at the same document, multiple documents that are similar, and common data or metadata across a set of documents. As the customer moves up the maturity curve, the DSG suggests process simplifications and/or improved ways of doing business to achieve greater process maturity. As the DSG processes more documents related to the medical office and/or the medical industry, the tools utilized by the DSG also improve to increase the DSG maturity level as well. The result is a service to provide a medical office with automated processing of documents of expected types. Automatic processing may include, for example without limitation, image clean up, OCR if necessary, identification of document type, extraction of metadata from documents, certifying images as having not been altered from the original document, and the mapping of metadata and image files into an appropriate taxonomy for medical services. The DSG may be trained to recognize documents related to various components of a medical office setting, such as patient records, office expenses, government compliance, and the like and, further, extract corresponding metadata therefrom in accordance with the training.

Patient records, by way of example, may include documentation for Medicare, living wills, power of attorney, organ donor cards, release forms, from which metadata such as patient name, date, blood type, allergies may be extracted. Further, patient records may include documentation such as insurance cards, doctors notes, prescriptions written, tests ordered and corresponding test results, insurance documents submitted and corresponding insurance documents received, payments received, patient visits, etc., from which appropriate metadata is extracted (e.g., patient ID, test names, lab information, prescription information such as dosage, quantity, name, and refills, insured ID, insurer information, account balance, appointment date and time, missed appointments, etc.). In either scenario, the appropriate metadata is extracted and mapped into the data repository. Further, the system is adapted to meet and comply with emerging government standards for Electronic Medical Records (EMR) such as, for example, the Continuity of Care Record (CCR) standard, which facilitates the timely sharing of a patient's health information between various caregivers.

Office expenses, for example, may include documentation such as supplies, suppliers, rent, utilities, equipment rental, employee payroll, etc. In this scenario, metadata related to office expenses may include, for example, date of purchases, billing dates, due dates, payment sent, amount past due, and the like. Metadata related to employee payroll may include, for example, employee payroll number and ID, gross pay, deductions, net pay, payment dates, and the like. In either scenario, the appropriate metadata is extracted and mapped into the data repository.

Government compliance, for example, may include documentation such as Sarbanes Oxley and HIPPA forms which the DSG automatically recognizes and extracts appropriate metadata therefrom. The DSG maps the documentation and/or the corresponding metadata into the data repository.

In use, a customer uses a standard web browser to connect to the Internet (e.g., using a PC, a cell phone, handheld device, etc.). Using a device to digitize paper documents (e.g., a standalone scanner or a scanner as part of a multi-function device, a cell phone camera, etc.), the customer digitizes documents for uploading, via the web browser, to the DSG. Customers may also upload electronically created documents. The DSG hosts client software that is utilized through downloadable plug-ins to provide iconic access to the data repository on the hosted server. The customer may utilize one or more icons and/or shortcuts on the desktop of their PC or the interface of a computing device to upload documents (e.g., via drag and drop), review uploaded documents processed by the DSG for purposes of verification and/or correction, and receive notifications, discussed in further detail below. Further, an icon and/or shortcut on the desktop or interface is provided to facilitate access to the data repository on the hosted server to view their stored data. The view of the data repository for a given customer may be dictated by customer preference and/or the specific business and/or industry (e.g., legal, accounting, customer service, etc.) in which the customer is involved.

Figure 1:
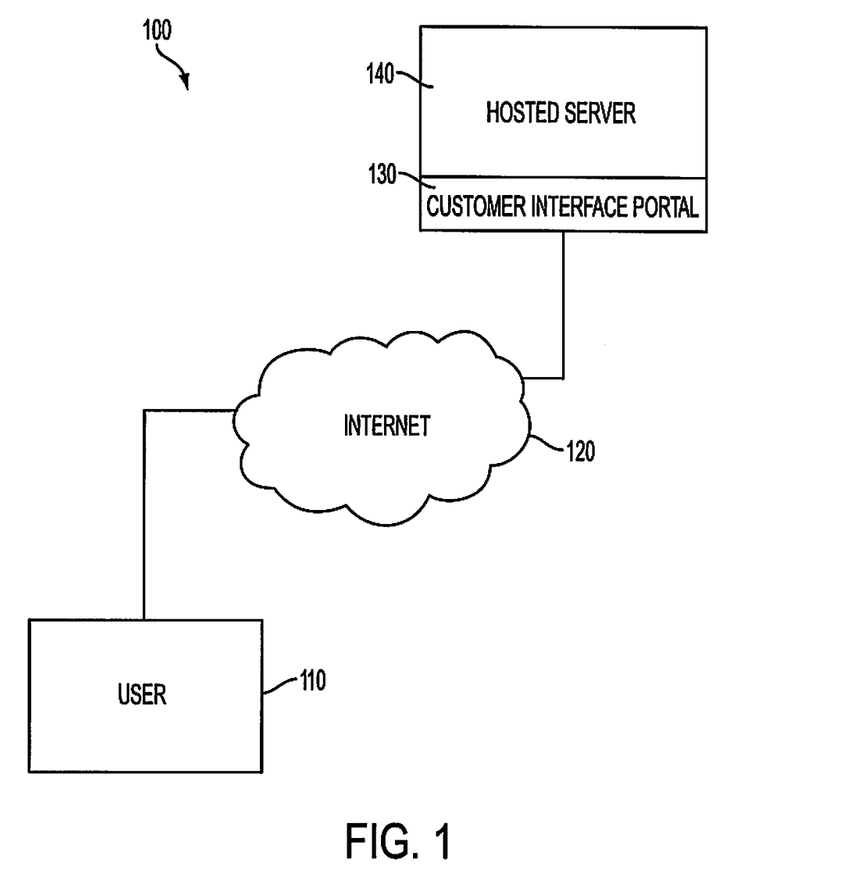
FIG. 1 is a block diagram of a general framework for implementing a scaleable web-based business service using document processing in accordance with the present disclosure.

Referring now to FIG. 1, a business services system 100 adapted for providing services to a medical office is shown and generally includes a hosted server 140 accessible by a user 110 over the Internet 120 through a customer interface portal or scaleable business services website 130 ("SBS website 130"). The term "users", as referenced herein, may refer to one or more employees, agents, and/or proprietors of the medical office such as a nurse, a doctor, an administrative assistant, an office administrator, etc. The SBS website 130 may be, for example, an Internet-based hosted service (e.g., Web 2.0®) accessed over the Internet 120 via a customer web portal. Using a standard web browser, the user 110 may connect to the Internet 120 to access the data repository on the hosted server 140 through the SBS website 130. With this purpose in mind, the user 110 may utilize a PC and/or any suitable web-enabled handheld device (e.g., phone) to connect to the SBS website 130. Customer software requirements are minimal in that plug-ins may be used to provide iconic access to the hosted server 140 through the SBS website 130. In this way, medical offices do not need to purchase, configure, or maintain their own software.

Utilizing a suitable scanning device (not explicitly shown) such as, for example, a scanner, a digital camera, or a cell phone camera, the customer or user 110 digitizes documents for uploading to a data repository on the hosted server 140. In a practical setting, the medical office would have a scanning device readily available in appropriate areas of the office. For example, a front desk area or reception area could include a scanning device to handle documents produced by patients as they arrive and depart the office. Other scenarios related to scanning device placement in the medical office are contemplated and the above described scenario should not be construed as exhaustive.

Suitable security mechanisms such as encryption (e.g., secure sockets layer or transport layer security) may be used to secure a connection between the user 110 and the hosted server 140. In this manner, any documents or data communicated to or from the hosted server 140 may be encrypted to ensure that customer information is kept private. Documents may include, for example without limitation, electronic documents, image files from a multi-function device ("MFD"), and image files from a camera phone or digital camera. In embodiments, the DSG is adapted to receive image files transmitted from an MFD or cell phone camera directly. The hosted server 140 may be any suitable network device running any known operating system and configured to communicate data over a network (e.g., the Internet 120). In other words, a computer, switch, router, gateway, network bridge, proxy device or other network device that is programmed or otherwise configured to operate as explained herein is considered an embodiment of this disclosure.

Figure 2:
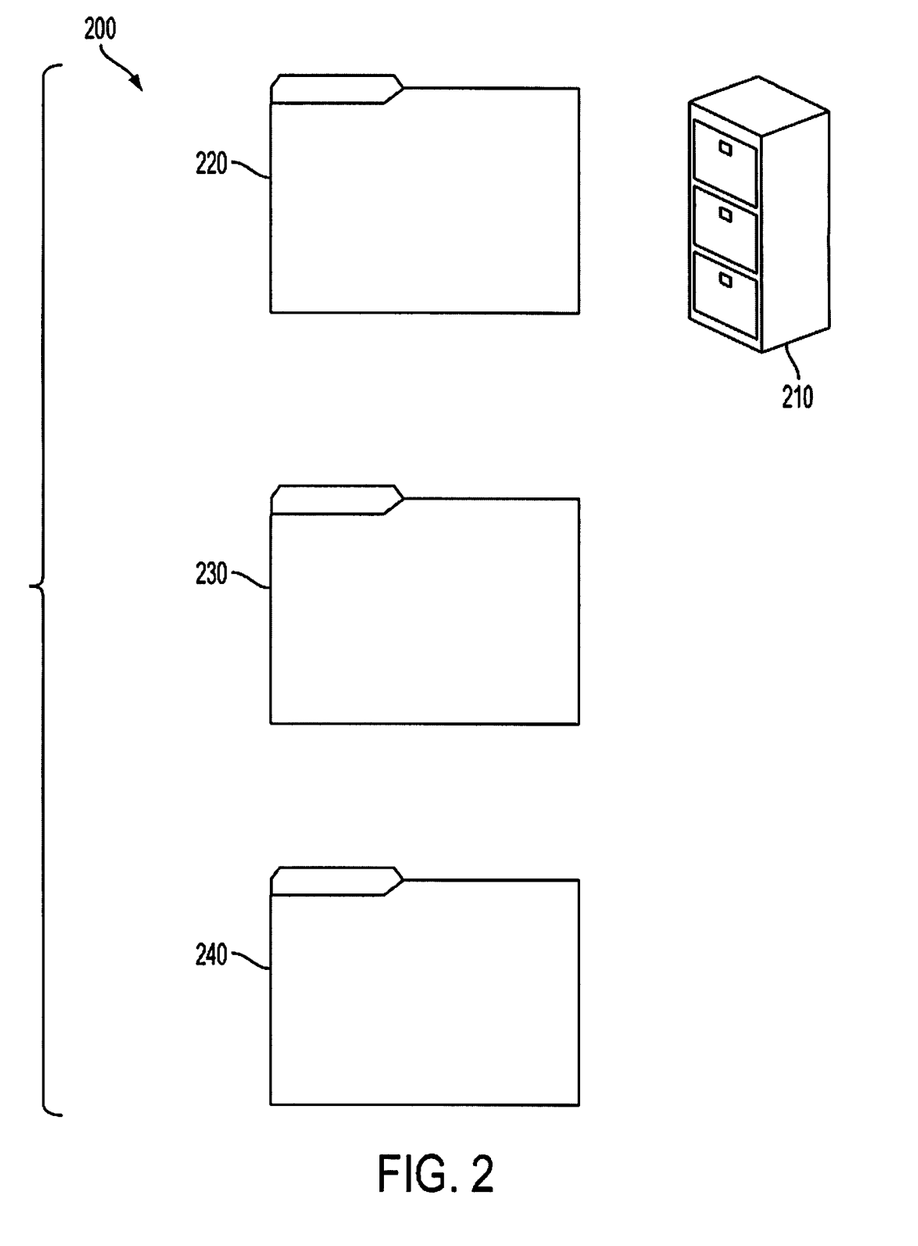
FIG. 2 is a sample view of a user interface for use with the web-based business service in accordance with embodiments of the present disclosure.

With reference to FIG. 2, a sample view or interface 200 of a user's display device (e.g., hand held device, intelligent phone, PC, etc.) is shown to illustrate how the user 110 may communicate and/or interact with the DSG from the medical office, as described in further detail below. Users 110 transfer (e.g., drag and drop) their documents and/or electronic images into the appropriate folder or shortcut on their interface 200. For example, in the illustrated embodiment, customers are provided with one or more folders and/or shortcuts. Customers have a customized view of the data repository based on their preferences or a default view optimized for a medical office.

In a practical setting, for example, a nurse or office administrator scans paper documents directly into the in basket 220 (e.g., using a scanning device, a cell phone camera, etc.) or, alternatively, scans paper documents onto their desktop or interface and drags and drops the scanned documents into the in basket 220 whereupon the transferred documents are automatically and securely transmitted to the data repository on the hosted server 140. Utilizing a suitable software application, the hosted server 140 automatically classifies the transferred document(s) and extracts essential metadata therefrom. For example, the host server 140 may employ a suitable processing software application having optical character recognition ("OCR") functionality to process uploaded files and extract key data therefrom for storage in the data repository. Typically, software applications utilized to seek out data from unstructured or semi-structured documents require "training" with sample sets of documents. This training enables the processing software application to recognize key data (e.g., text, data glyphs, bar codes, Optical Mark Recognition, logos, connected components, etc.) on a given document to classify the document and, based on this classification, seek out and extract data therefrom. Typically, documents related to a medical office setting are semi-structured and include key words and information that the processing software application may be trained to detect and extract. The processing software application is "trained" with sample sets of documents and documents related to the medical office setting, thereby enabling the classification of documents and extraction of customer-specific data therefrom. In embodiments, the processing software application may be trained with semi-structured documents that are well-known in the medical office industry to limit the complexity and costs associated with automating the DSG. In the event that the DSG fails to classify a document or wrongly classifies a document, the customer may correct the results, accordingly. That is, if a document is not recognizable by the DSG or the DSG makes a self-determination that it is below a certain predetermined confidence threshold for classifying documents, the customer may verify and/or correct results to retrain the DSG and, thus, improve the confidence of the DSG with respect to a particular type or class of document. Likewise, the customer may verify that documents have been correctly classified and/or the metadata extracted therefrom is correct. With each document successfully classified, verified, and/or corrected, the accuracy of the processing software application improves with respect to recognition and classification of documents. Further, the DSG is provided with knowledge and/or regulatory compliance for the medical industry and is able to detect and tag documents accordingly.

Opening or selecting the in-basket 220 reveals information such as a listing of documents currently being classified and document status (e.g., "finished", "review", etc.). Opening or selecting a review folder 230 on the interface 200 allows the user to review documents classified by the DSG and select specific documents to view information such as the document image, the document classification, and any metadata extracted from the document(s). The customer may verify any of the above-listed information and/or correct any errors made by the DSG during processing. In this manner, the DSG is re-trained with verified and/or corrected information relating to specific documents and/or classifications of documents. For example, if the processing software application is unable to extract data from a document and/or classify the document with certainty, the customer is alerted through the review folder 230. The customer may verify the classification of the document and/or the data from the document and, further, make corresponding modifications. Further, the DSG is self-learning in that each successful classification and extraction of a document enables the DSG to accumulate a so-called "knowledge-base" of documents specific to the medical office setting. In this way, the DSG matures with each document classified, whether successfully or unsuccessfully and subsequently verified and/or modified. That is, once a document or document type has been verified, subsequent documents of the same or substantially similar type may not require verification by the customer thereafter. Classified and verified documents are stored in the data repository of the hosted server 140.

Based on key data extracted from classified and/or verified documents, the DSG is adapted to automatically generate service or business suggestions (e.g., computing and/or connectivity upgrade suggestions based on business volume), document summarizations, document redacting, notifications, events, progress, offers, and the like. The customer may receive any of the above discussed customer-specific information (e.g., via email or any suitable method) on demand and/or periodically in accordance with the preference of the customer. A suitable software application (e.g., content management software) operating on the host server 140 is adapted to process digital images. The content management software may include, for example, a services-specific application adapted to provide document or information related technologies such as image clean up, data extraction (e.g., optical character recognition), image classification, image classification vs. text classification, amount of color usage, and data mining. Further, the services-specific application is adapted to provide document category sets, workflows and routings, regulatory rules, and service links to customize the service according to a medical office setting. The content management software may also include, for example, a customer-specific application adapted to process and store images and/or data uploaded by the user 110 such as, image files, metadata related to the image files, unique classification rules specific to the medical industry, customizable permissions, and/or notifications of events and/or triggers related to data stored for a customer.

The customer may view their documents stored in the data repository of the host server 140 by selecting a repository icon 210 on their interface 200 to access the data repository via the SBS website 130, as will be discussed in further detail below with reference to FIG. 3. In this manner, the customer is able to perform various tasks such as, for example, searching for documents, producing and/or subscribing to reports, viewing image files, and viewing metadata related to documents. Further, the customer is able to arrange to receive reports and notifications related to the medical office and/or the medical industry. A reports folder 240 on the customer interface 200 may be selected to view reports to which the customer has subscribed and/or produced.

Reports are predefined and the customer may choose to view the reports or not. Reports may include information helpful to the customer in running their business such as, for example, tracking bills and payments, summaries of year-end tax documents, reminders, compliance information, reports, work process information, alerts from user to user regarding responsibility for work flow steps, information updates (e.g., from an RSS feed or a Mashup), and the like. In a practical setting, by way of example, daily reports may include scheduled appointments, supplies in need of ordering, and equipment that needs servicing. Weekly reports may include, for example, payments due within the week and scheduled appointments for the week. Monthly reports may include, for example, payments due, payments made, monthly expense summary, and pending expiration of office equipment warranties. Annual reports may include, for example, tax support documents arranged by tax subject area, expenses identified and exportable to tax software applications, images available for support, and payroll summary. Further, reports may be generated on-demand by the customer as needed.

Notifications are provided from the DSG to the medical office by email, text message, pop-up window on the SBS website 130, or any suitable medium of remote data transfer. Notifications are provided to the customer as a reminder of matters that may require more immediate attention than matters related to reports in the reports folder 240. By way of example, a notification may be a reminder of reports that are available in the reports folder 240, payments due immediately or in the immediate future (e.g., less than a week), payments overdue, warranties expiring in the immediate future, receivables overdue, and the like.

Through the SBS website 130, the customer may learn about available services, test available services, and register for available services (e.g., through use of a wizard). For example, the SBS website 130 may include website links to tools or services useful for a medical office and/or forms and information websites (e.g., health advisories, CDC, legal advice, tax forms, etc.). Further, the customer may select desired services, identify document classifications utilizing samples to train the DSG, identify desired notifications, run sample sets and check results, select reports to view or download, etc. The SBS website 130 also provides hints and/or tips for correcting misclassified documents or misinterpreted data.

Customers may subscribe to any one or more industry-specific and/or business-specific services offered by the DSG under various payment or subscription fee models. For example, customers may only be required to pay for the services they use and not be obligated to a subscription contract. Alternatively, the customer may be required to pay a one-time subscription fee and/or a periodic subscription fee. Customers that wish to cancel a service to which they have subscribed, are given a computer-readable medium (e.g., CD, DVD) having stored thereon the customer's documents and/or data including a tool to view and export the data.

Figure 3:
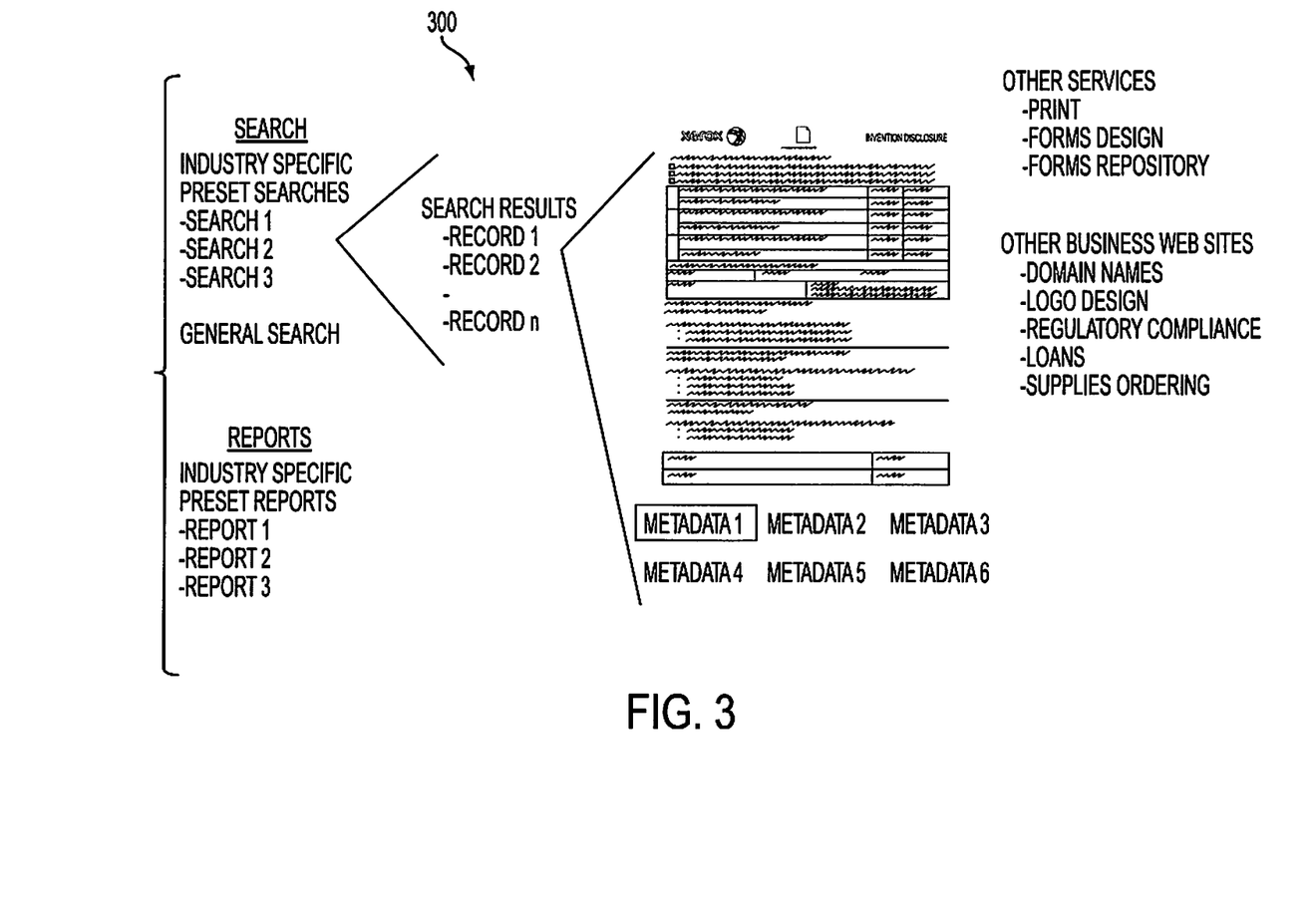
FIG. 3 is a sample customized user view of a web-based interface of the business service in accordance with embodiments of the present disclosure.

FIG. 3 shows a sample customized user view on the SBS website 130 to illustrate how a customer may search for and view processed documents stored on the data repository. The view, referenced generally as 300, may be customized by the customer to suit the needs of the medical office or a default view may be used that is optimized for a medical office setting to facilitate intuitive interaction between the medical office and the SBS website 130. Upon selection of the repository icon 210 (FIG. 2), the user 110 connects to the SBS website 130 via the Internet 120 to access the repository on the host server 140. In use, the user 110 is authenticated utilizing a suitable software application (e.g., user name and password) before gaining access to their documents and/or their custom view 300. As shown in FIG. 3 by way of example, the custom view 300 lists reports available to the user 110, search results, customer services (e.g., document printing, document form design, document form repository, etc.), and service links to useful business services related to the medical industry (e.g., domain names, logo design, regulatory compliance, loans, supplies ordering, etc.). Service links may be provided to facilitate access to other types of document services available in a relatively traditional format such as, for example, mass mailing services for distributing newsletters, HIPPA compliance letters, mail advertisements, health advisories, and the like. Service links to attorney services may also be provided. Other information specific to the medical industry may be available to the user 110 and the above list should not be construed as exhaustive.

Figure 4:
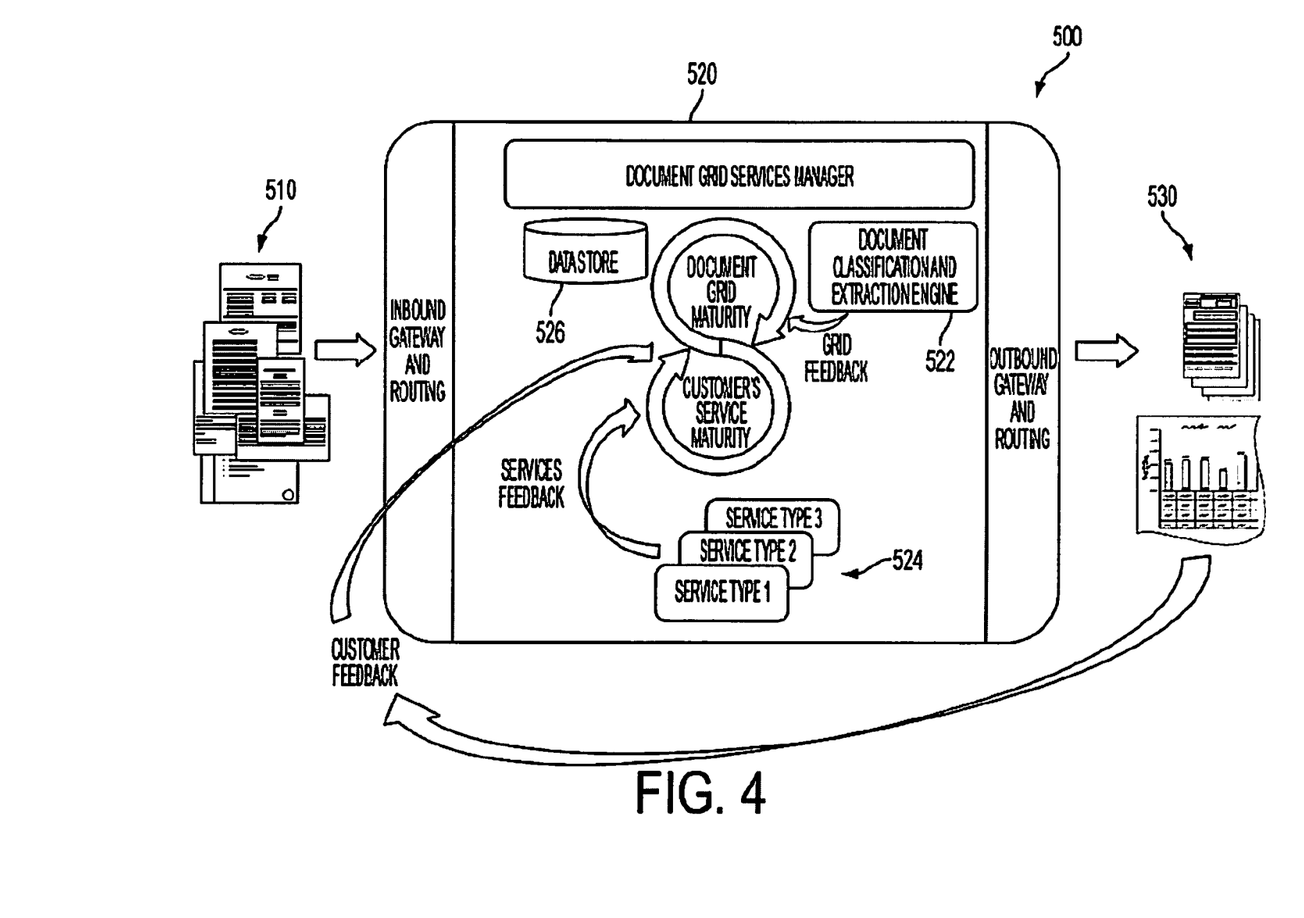
FIG. 4 shows the system architecture of a document services grid in accordance with embodiments of the present disclosure.

FIG. 4 illustrates system architecture of the DSG in accordance with embodiments of the present disclosure and is referenced generally as 500. The DSG system 500 includes a DSG manager 520 operating, for example, on the host server 140 (FIG. 1). The DSG manager 520 is adapted to receive customer documents 510 through inbound gateways and/or routing (e.g., eMail, Fax, MFD, Web Folder, etc.). Customer documents 510 may be stored in a storage device or repository 526. Customer documents 510 may be accepted by the DSG manager 520 in any order and in any one of a variety of suitable file or document formats. The DSG system 500 allows for ad-hoc document input using intuitive input and output gateways to the DSG manager 520 such as, for example without limitation, drag-n-drop, email, fax, and network scan. Further, the DSG system 500 provides a document classification and extraction engine 522 to extract and process key data from documents utilizing specialized or trained document classification and extraction technologies. Based upon extracted data, the DSG manager 520 generates business data output 530 targeted at the medical office using outbound gateways and routing. In this manner, the DSG manager 520 performs, rather than the customer, processing and labor-intensive work related to documents and the data extracted therefrom. Further, the DSG manager 520 generates archival versions of original input documents stored in the repository 526 to ensure document integrity as well as Sarbanes Oxley compliance. In embodiments, the DSG system 500 may store and/or display documents in a common, normalized format (e.g., PDF).

The system 500 is built on so-called "dual-mode dynamic maturity model" engine. More specifically, one mode of the system 500 allows individual services 524 to be managed or offered at different maturity levels concurrently. Another mode of the system 500 allows the maturity of the system as a whole to be managed independently. The system 500 as a whole offers multiple feedback loops (e.g., services feedback from individual services 524, grid feedback from the document classification and extraction engine 522, etc.) and refinement tools to grow the maturity of the medical office service offered by the DSG system 500 as well as the DSG system 500 as a whole. This configuration allows the customer to improve their return on investment and enables the administrator of the DSG system 500 to improve efficiency of delivery to effectively provide the complete lifecycle for document processing and related services.

The DSG framework 500 may be embodied as a grid computing system that combines the network, storage, computing, and software elements to provide centralized processing power to the medical office and, moreover, to achieve a scaleable solution. The medical office connects to and utilizes the centralized processing power of the grid computing system to execute document processing related to the medical office industry.

In embodiments, a variety of authentication mechanisms (e.g., username, password, etc.) may be employed to prevent unauthorized access to the DSG. In this scenario, authenticating information such as, for example, a username and password is required to access the hosted server 140. In embodiments, the data repository may store documents and related data as digital image files (e.g., JPG, GIF, PNG, TIF, etc.) or as PDF files in the repository to provide archive protection. In this manner, the DSG may offer a guarantee that uploaded documents will not be altered once received and processed by the hosted server 140.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A document processing method for a medical office, comprising:
    receiving, at a server with a network interface, electronic documents including patient records, office expenses, and government compliance from a medical office, the server including a software application adapted to recognize an expected class of each electronic document;
    processing the each electronic document received from the medical office based on the recognized class to extract data therefrom;
    automatically mapping the extracted data from the first processed electronic document to a data repository on the server, the data repository being accessible by the medical office through the network interface;
    electronically generating at least one of a service and business suggestion on a routine basis to the medical office, the suggestion being directed toward a medical office setting and being based on at least one of the mapped data on the data repository and process maturity indicators, the output data corresponding to at least one of a process simplification and improvement to achieve greater process maturity.

2. A method according to claim 1, wherein electronically generating the output data to the medical office includes generating at least one report corresponding to operation of the medical office, the at least one report being accessible by the medical office via the network interface.

3. A method according to claim 2, wherein the at least one report corresponds to at least one of patient records, office expenses, and government compliance.

4. A method according to claim 2, wherein the at least one report is accessible to the medical office via iconic access through the network interface.

5. A method according to claim 1, wherein a plurality of service links are accessible to the medical office through the network interface, the service links being linked to web-based information related to operation of the medical office.

6. A method according to claim 1, wherein electronically generating the output data to the medical office includes generating at least one notification to the medical office, the at least one notification configured to remind the medical office of a matter relating to operation thereof.

7. A method according to claim 6, wherein the at least one notification is provided to the medical office via at least one of email, text message, and pop-up window.

8. A method according to claim 1, wherein the data repository is accessible to the medical office via iconic access through the network interface to facilitate viewing of the at least one processed electronic document.

9. A method according to claim 1, wherein processing of electronic documents includes at least one of image clean up, OCR, identification of document type, extraction of metadata, certification, and automatic mapping of metadata to the data repository.

10. A method according to claim 1, wherein the process maturity indicators corresponds to at least one of a frequency with which the medical office accesses particular mapped data, a processing of a plurality of electronic documents that are substantially similar, and a mapping of common data from a plurality of processed electronic documents.

11. A method according to claim 1, wherein the output data generated includes information corresponding to improving operation of the medical office.

12. A method according to claim 1, wherein the data repository stores the at least one processed electronic document in a protected archive to facilitate government compliance of the medical office.

13. A document processing system for a medical office, comprising:
   a document services grid accessible through a network interface and adapted to receive electronic documents of classes including patient records, office expenses, and government compliance from a medical office through the network interface, the document services grid comprising:
      a hosted server including a software application adapted to recognize a class of each electronic document and extract data from the each document based on the recognized class; and
      a data repository operating on the hosted server and configured to store data automatically mapped from the each electronic document, the mapped data also corresponding to a process maturity indicator based on monitoring of the medical office, wherein the document services grid is configured to generate output data to the medical office based on the mapped data,
   the document services grid being further adapted to train the software application to recognize each class based on the mapped data of at least a first electronic document and subsequently process at least a second electronic document that is substantially similar to the at least one electronic document based on a recognition of the class, the document services grid being further adapted to output at least one of a service and business suggestion directed toward a medical office setting being related to a data process simplification to achieve greater process maturity;
   wherein the network interface receives from the medical office one of a verification and a correction of the mapped data to train the software application based on one of the verification and the correction such that the second electronic document is automatically recognized based on the first electronic document.

14. A document processing system for a medical office according to claim 13, wherein the data repository is remotely accessible by the medical office through the network interface.

15. A document processing method for a medical office, comprising:
   receiving, at a server, at least one electronic document from a medical office, the server being hosted on a document services grid accessible through a network interface and including a software application adapted to recognize an expected class of each electronic documents corresponding to patient records, office expenses, and government compliance at the medical office;
   extracting data from the each electronic document received from the medical office through the network interface based on the recognized class;
   automatically mapping the extracted data to a data repository on the hosted server;
   monitoring a process maturity indicator of the medical office based on access to the mapped data of at least two documents; and
   electronically generating at least one report based on at least one of the mapped data and the monitored process maturity indicator, the at least one report corresponding to at least one process simplification to improve process maturity of a medical office setting, and the report being made accessible via the network interface;
   providing the medical office with access to the mapped data for receiving one of a verification and a correction to train the software application based on one of the verification and the correction; and,
   automatically classifying a subsequently processed electronic document that is substantially similar a previously verified electronic document to train the software application in accordance with the class of the previously recognized electronic document.

16. A method according to claim 15, wherein the at least one report is accessible to the medical office via iconic access through the network interface.

17. A method according to claim 15, further comprising: generating at least one notification to the medical office, the at least one notification configured to remind the medical office of a matter relating to operation thereof.

18. A method according to claim 15, further comprising: extracting data from the at least one processed electronic document based on the recognition that the at least one electronic document belongs to the expected class of electronic documents corresponding to the medical office.

19. A method according to claim 1, further comprising:
   providing the medical office with the mapped data on the data repository via a network interface;
   receiving one of a verification and a correction of the mapped data;
   training the software application using the one of the verification and the correction for recognizing a document belonging to the class of documents; and,
   automatically classifying a subsequently processed electronic document that is substantially similar to a first electronic document from which the mapped data has been the one of verified and corrected to train the software application in accordance with the class of the previously processed first electronic document.

* * * * *